United States Patent [19] [11] 3,969,205
Kawamura et al. [45] July 13, 1976

[54] PROCESS FOR PRODUCING 2-CHLOROPYRIDINE

[75] Inventors: Masao Kawamura, Akashi; Tadaaki Nishi, Kakogawa; Syuzi Takagi, Akashi, all of Japan

[73] Assignee: Seitetsu Kagaku Co., Ltd., Japan

[22] Filed: Dec. 6, 1974

[21] Appl. No.: 530,563

[30] Foreign Application Priority Data

Dec. 8, 1973   Japan............................. 48-139851

[52] U.S. Cl.......................................... 204/158 HA
[51] Int. Cl.$^2$............................................ B01J 1/10
[58] Field of Search .............................. 204/158 HA

[56] References Cited
UNITED STATES PATENTS 3,297,556   1/1967   Boudakian et al. ........... 204/158 HA Primary Examiner—Howard S. Williams
Attorney, Agent, or Firm—Pollock, Vande Sande & Priddy

[57] ABSTRACT

Pyridine is reacted with chlorine in the presence of water by photolytic reaction under irradiation of photolytic light, using halogenated hydrocarbon such as carbon tetrachloride as a diluent. When the amount of water added exceeds at least 0.01 moles per one mole of pyridine, an effect of water addition appears, but usually addition of 0.2 to 10 moles, preferably 0.5 to 5 moles of water per one mole of pyridine makes the reaction proceed smoothly without any trouble, and ensures increase in yield and selectivity of 2-chloropyridine. The present process can be carried out in either gaseous or liquid phase.

15 Claims, No Drawings

PROCESS FOR PRODUCING 2-CHLOROPYRIDINE

This invention relates to an improvement in a process for producing 2-chloropyridine from pyridine and chlorine, using photolytic light.

2-Chloropyridine is useful as raw materials for agricultural chemicals, pharmaceutical chemicals and other industrial chemicals.

Heretofore, several processes have been proposed for producing 2-chloropyridine from pyridine and chlorine, and these processes can be classified into two major groups, that is, processes for carrying out thermal reactions at an elevated temperature and processes for carrying out photolytic reaction under irradiation of ultraviolet rays.

Examples of the former thermal reaction are disclosed in U.S. Pat. Nos. 2,820,791 and 3,153,044 where pyridine reacts with chlorine in the presence of water or carbon tetrachloride as a diluent at an elevated temperature such as 260° to 420°C. Thus, not only selection of corrosion-resistant materials of construction is an important problem in the practice of the processes in an industrial scale, but also hardly separable or removable by-products and 20 to 50 % of tarry matters are inevitably contained in the resulting reaction product, and cause clogging of reactor or conduits, rendering continuation of the reaction difficult. Furthermore, a risk of combustion of pyridine in the reaction system or explosion cannot be completely eliminated in the reaction at the elevated temperature, even if a diluent is used.

An example of the latter process for photolytic reaction is disclosed in U.S. Pat. No. 3,297,556, where pyridine reacts with chlorine in a liquid or gaseous phase under irradiation of light to product 2-chloropyridine. In the photolytic process, the reaction temperature is so low that improvements are made as to the difficulty in selecting materials of construction and the risk of explosion. When the photolytic process is carried out in a liquid phase, halogenated hydrocarbons or pyridine is used as a diluent, and the reaction is carried out at a boiling temperature, but in this case, hydrochloric acid by-produced with the progress of the reaction reacts instantaneously with pyridine in the reaction system, thereby forming and crystallizing out hydrochlorides in the reaction solution, and the hydrochlorides deposit on surfaces of chlorine gas feeding pipe, reactor, or condenser on the reactor, and clogging the reactor or pipes. Thus, continuation of reaction becomes impossible. When pyridine is used as a diluent, pyridine is expensive, and thus economically disadvantageous, and furthermore forms solid addition compounds with chlorine, causing cloggings. Furthermore, when the hydrochlorides deposit on the surface of irradiation light source, they are formed into tarry matters by the ultraviolet rays, making light transmission difficult. It is also disclosed as an example that crystallization of solids is suppressed by adding a very small amount of water to a largely excessive amount of pyridine (pyridine itself is used as the diluent), but the yield of 2-chloropyridine is very low, for example, 12.8 %. There is also disclosed a reaction example using only water as the diluent [J. Heterocyclic Chem., 4 375 (1967)], but its yield is 7.3 %, and according to experiments conducted by the present inventors, it is found that reaction of chlorine with water to form hydrochloric acid takes place in preferance to formation of 2-chloropyridine, and 2-chloropyridine is hardly formed.

In said U.S. Pat. No. 3,297,556, it is disclosed that said photolytic reaction is carried out in a gaseous phase using carbon tetrachloride as a diluent. However, according to the experiments conducted by the present inventors it is found in said gaseous phase photolytic process, that considerable amount of tarry matters and other by-products attach to wall surfaces of reactor tube, rendering light transmission difficult, and causing clogging of a conduit for withdrawing the product mixture, as in the liquid phase reaction. Thus, it is hard to continue the reaction.

An object of the present invention is to provide an improved process for producing 2-chloropyridine in high yield free from any risk of explosion by carrying out photolytic reaction of pyridine with chlorine in a liquid phase or vapor phase under irradiation of ultraviolet rays.

Another object of the present invention is to provide an excellent photolytic process completely free from any trouble of inhibition of light transmission or conduit clogging caused by attachment of tarry matters and other by-products by suppressing tar and by-product formation side-reaction.

Other object of the present invention is to provide a process for continuously producing 2-chloropyridine readily in an industrial scale especially by a gaseous phase photolytic reaction.

As a result of extensive studies on eliminating said disadvantages of the prior art processes and attaining said objects, the present inventors have found that photolytic reaction of pyridine with chlorine can be carried out in high yield with high selectivity without any risk of explosion if a mixture of pyridine with chlorine is subjected to the reaction in the presence of water. Though details of actions attained in the present invention have not been completely clarified yet, it seems that tarry matters, by-produced hydrochlorides, etc. attaching to wall surfaces of reactor absorb water reaction system to form an aqueous hydrochloride solution. In the liquid phase reaction, the aqueous hydrochloride solution is formed as a liquid layer over the reaction solution, and makes the wall surfaces of the reactor clear, or water azeotropically boiling together with halogenated hydrocarbon dissolves the hydrochloride attaching to the surfaces of the reactor and condenser and prevent the clogging of the reactor and condenser completely. In the gaseous phase reaction, the aqueous hydrochloride solution wets the wall surfaces of the reactor. The resulting aqueous hydrochloride solution is readily discharged to the outside of the reactor together with the reaction gas mixture, keeping the wall surfaces of reactor always clear. Thus, in the present invention no troubles of fouling of the light source jacket pipe and reactor caused by adhesion of the tarry matters and other by-products thereto and clogging of pipes are observed at all, and the reaction can be continued smoothly without any trouble.

In the present invention, pyridine and chlorine are used in the well known molar ratio, that is, a molar ratio of pyridine to chlorine of 0.5 – 10 : 1, preferably 1.5 – 5 : 1, more preferably 2 – 3 : 1.

Examples of halogenated hydrocarbons used as the diluent in the present invention include carbon tetrachloride, perchloroethylene, trichloroethylene, tetrachloroethylene, ethane dichloride, ethane trichloride, tetrachlorodifluoroethane, etc. In the present invention, 0.5 to 15 moles, preferably 2 to 10 moles of at least one of these halogenated hydrocarbon diluents is used per one mole of pyridine.

In the present invention, reaction is carried out in a reaction system consisting of said raw materials and a diluent in the presence of water. When at least 0.01 mole of water is added to the reaction system per one mole of pyridine, an effect of addition of water appears, but usually it is desirable to keep a sum total of water and halogenated hydrocarbon in a range of 1 to 20 moles per one mole of pyridine; in a range of 0.2 to 5 moles, preferably 0.5 to 3 moles per one mole of pyridine in the case of liquid phase reaction and in a range of 0.2 to 10 moles, preferably 0.5 to 5 moles per one mole of pyridine in the case of gaseous phase reaction. If the amount of water is too small, the by-produced pyridine hydrochloride deposits on the inner wall of the reactor or outlet pipe of condenser, etc. and inhibits light transmission or causes cloggings. That is, the effect of addition of water is lesser. When the amount of water is too large, reaction of chlorine with water to form hydrochloric acid takes place in the liquid phase reaction, as mentioned above, and no more 2-chloropyridine is formed. In the case of gaseous phase reaction, there takes place no inhibition of reaction, but purification and separation of the resulting reaction products become complicated, and the loss of unreacted pyridine due to dissolution will be increased.

In the present invention, water can be added to the reaction system in any manner. In the case of liquid phase, tank-type batch reaction, all the amount of water can be charged into the reactor before the reaction, or water can be fed to the reactor at a definite rate together with chlorine gas. When the reaction is carried out continuously in a liquid phase, water is usually mixed with pyridine, and fed to the reactor, or water is continuously fed to the reactor during the reaction. When the reaction is carried out in a gaseous phase, water and raw materials are separately vaporized, and then led to a reactor, or water is led to a reactor by making water flow down along an inner wall of a reactor, and vaporizing the water while the water flows down. However, it is preferable to mix water with the raw material pyridine at said mixing ratio, pass the resulting mixture through an appropriate vaporizer, thereby vaporizing the mixture, lead the resulting gaseous mixture of pyridine and steam to a reactor and react the pyridine with chlorine gas therein.

Furthermore, chlorine is usually fed to the reactor in a gaseous state, but when the reaction is carried out in a gaseous phase, yield and selectivity are increased by mixing the chlorine gas with gaseous halogenated hydrocarbon and feeding the resulting mixture to the reactor, because the reaction can be carried out uniformly.

In the present invention, reaction can be carried out in both gaseous and liquid phases, using said raw materials, diluent and water, but the process most suitable to an industrial application is such that a mixture of pyridine and water, and chlorine or a mixture of halogenated hydrocarbon and chlorine are continuously charged in a gaseous phase into a reactor and subjected to photolytic reaction under irradiation of ultraviolet rays of 2,000 to 5,000 A from an outside or inside light source. Particularly, in the present invention, it is more efficient and convenient to use a reactor provided with a light source of inside irradiation type.

Any lamp can be used as a light source in the present invention, so long as the lamp can emit ultraviolet rays, and a high pressure mercury lamp can be usually used.

The resulting product mixture is condensed or cooled, depending upon the case and the condensate can be readily purified according to the well known procedures, for example, by a combination of neutralization, extractive separation and distillation, as disclosed in U.S. Pat. Nos. 2,820,791 and 3,153,044.

In the present invention, it is advantageous for industrial scale production to employ a gaseous phase process, which is readily practicable in a continuous manner.

Now, the present invention will be hereunder described in detail, referring to examples, but the present invention is not limited to these examples.

EXAMPLE 1

Into a glass reactor (capacity: 10 l; inner diameter: 250 mm; depth: 250 mm) provided with a stirring rod, thermometer, chlorine feeding pipe, mercury lamp (450 W) Type UM-452 made by Ushio Denki K.K., Japan, having Pyrex glass cooling tube for light source, and condenser were charged 13,881 g of carbon tetrachloride, 714 g of pyridine and 150 g of water, and the inside temperature of the reactor was maintained at 76°C. Then, 320 g of chlorine gas was fed to the reactor under irradiation of ultraviolet rays over a period of one hour, and subjected to reaction. In the course of reaction, no inhibition of reaction by tar or by-produced hydrochloride was observed. The reaction product solution was separated into two layers, i.e. an aqueous layer and an organic layer. Analysis of these two layers revealed that 261.2 g of 2-chloropyridine was obtained, its yield was 25.5 % by mole on the basis of the charged pyridine, and 11.2 g of 2,6-dichloropyridine was contained in the reaction product solution.

Purified 2-chloropyridine boiled at 102°C under 100 mmHg, and had a refractive index, $n_D^{20}$ of 1.5318.

For comparison, reaction was carried out in the same manner as above, except that no water was used, but hydrochlorides were deposited on the surfaces of the chlorine feeding pipe, cooling tube for light source, condenser, etc. and continuation of the reaction became impossible.

EXAMPLE 2

Into the same glass reactor as used in Example 1, except that the capacity of the reactor was 1.5 l and the cooling pipe for light source in which a high pressure mercury lamp (100 W) made by Ushio Denki K.K. Japan, was inserted, was made from quartz, were charged 2,221 g of carbon tetrachloride, 143 g of pyridine, and 70 g of water to the reactor, and the inside temperature of the reactor was kept at 78°C.

Then, chlorine gas was fed to the reactor under irradiation of ultraviolet rays for 230 minutes, and subjected to reaction. The amount of chlorine consumed was 70 g. In that reaction, 39.5 g of 2-chloropyridine was obtained, and its yield was 19.2 % by mole on the basis of the charged pyridine.

EXAMPLE 3

Into the same glass reactor as used in Example 1 except that the capacity of the reactor was 500 ml, were charged 904 g of carbon tetrachloride, 47 g of pyridine and 10 g of water, and the inside temperature of the reactor was kept at 78°C. 21 g of chlorine gas was fed to the reactor over a period of one hour under irradiation of ultraviolet rays to gaseous phase zone, and subjected to reaction. In that reaction, 21.7 g of 2-chloropyridine was obtained, and its yield was 32.5 % by mole on the basis of the charged pyridine.

EXAMPLE 4

Into the same glass reactor as used in Example 1 were charged 14,400 g of trichlene, 714 g of pyridine, and 200 g of water, and the reactor was heated until the inside temperature of the reactor reached 85°C.

Then, chlorine gas was fed to the reactor at a definite feed rate under irradiation of ultraviolet rays for 2 hours, and subjected to reaction. The amount of chlorine consumed was 240 g. In that reaction, 225 g of 2-chloropyridine was obtained, and its yield was 21.9 % by mole on the basis of the charged pyridine. In the reaction product, the diluent trichlene and 2.8 % by weight of further chlorinated materials on the basis of 2-chloropyridine were contained.

EXAMPLE 5

Into the same glass reactor as used in Example 1 was charged 13,881 g of carbon tetrachloride, and the reactor was heated until the inside temperature of the reactor reached 78°C. Then, the high pressure mercury lamp was turned on, and after the lamp was sufficiently stabilized, 5.33 g/minute of chlorine and 2.5 g/minute of water were fed to the reactor by means of metering pumps, and subjected to reaction for one hour. Analysis of the resulting products revealed that 528 g of unreacted pyridine and 258 g of 2-chloropyridine were contained in the reaction product solution. Consequently, yield of 2-chloropyridine was 25.1 % by mole on the basis of the charged pyridine.

EXAMPLE 6

A glass pipe (inner diameter: 95 mm) provided with a high pressure mercury lamp, 100 W, Type UM-102, made by Ushio Denki K.K. Japan, was kept at 100°C, and carbon tetrachloride, and water were fed to the glass pipe from its top in a molar ratio of carbon tetrachloride : pyridine : water of 2.29 : 2.14 : 2.14 in a preheated gaseous state. On the other hand, chlorine gas was fed to the glass pipe at a molar ratio of chlorine : pyridine of 0.47 : 1, and subjected to reaction. The resulting reaction product was slightly yellowish, and no formation of tarry matters was observed. As a result of the analysis of reaction product, it was found that yield of 2-chloropyridine was 44.9 % by mole on the basis of fed pyridine.

For comparison, water ratio was lowered, and reaction was carried out at a molar ratio of water : pyridine of 0.2 : 1. Black spot fouling started to appear on the wall surfaces of reactor. As a result of the product resulting from the reaction for 20 minutes, it was found that yield of 2-chloropyridine was 25.4 % by mole on the basis of fed pyridine. Another reaction was carried out in the same manner as above, except that water was not fed to the glass pipe at all, but tarry matters were deposited on the light source-cooling pipe in the course of reaction, and also the conduit at the outlet of the glass pipe was clogged by deposited salts. Yield of 2-chloropyridine was 13.4 % by mole, on the basis of fed pyridine.

EXAMPLE 7

A light source-cooling pipe was fixed at the center of a glass-lined reactor with a jacket (reactor capacity: 43 l; inner diameter: 350 mm; length: 400 mm), provided with a pyridine-water mixture vaporizer, a carbon tetrachloride vaporizer, a chlorine feeding tube and a thermometer, and a high pressure mercury lamp, 2 KW, Type UML-D 2254, made by Ushio Denki K.K., Japan, was inserted into its center. Further, a glass cooler was provided at the bottom at the center of the reactor, and furthermore a 50-l receiver was disposed under the glass cooler. Uncondensed gas was made to be absorbed in an aqueous alkali solution.

At first, hot water at 80°C was circulated through the jacket of the reactor, and carbon tetrachloride was passed through the vaporizer and led to the reactor in a gaseous state at 100°C at a rate of 46.2 kg/hr. Then, the light source was turned on. Then, an equimolar solution of pyridine and water was passed through a vaporizer and led to the reactor at 120°C at a rate of 10.62 kg/hr. Then, chlorine gas preheated to 100°C was led to the reactor at a rate of 3.9 kg/hr through the carbon tetrachloride feeding pipe. Temperature of the reactor was immediately started to increase, and stabilized at 170°C. After the stabilization, the amounts of the raw materials and reaction products were exactly measured during the reaction for 20 minutes. The results are shown in Table.

For comparison, reaction was carried out in the same manner as above, except that pyridine was used in place of the equimolar solution of pyridine and water, but tarry matters were deposited on the light source-cooling tube in the course of reaction, and the outlet of the reactor was also clogged by black materials containing pyridine hydrochloride. As a result, yield of 2-chloropyridine from the fed pyridine was 12.5 % by mole.

Table

| Ex. No. | Amount fed (g) | | | | Molar ratio (based on pyridine) | | | | Formed 2-chloro-pyridine (g) | Formed 2,6-di-chloro-pyridine (g) | Reacted pyridine (g) | Yield (% by mole) | |
|---|---|---|---|---|---|---|---|---|---|---|---|---|---|
| | Pyridine | Water | Carbon tetrachloride | Chlorine | Pyridine | Water | Carbon tetrachloride | Chlorine | | | | Based on reacted pyridine | Based on fed pyridine |
| 7 | 2,880 | 650 | 15,410 | 1,300 | 2.0 | 2.0 | 5.5 | 1.0 | 1,480 | 100 | 1,120 | 92.0 | 35.8 |

What is claimed is:

1. A process for producing 2-chloropyridine by reaction of pyridine with chlorine in a molar ratio of pyridine to chlorine of 0.5 – 10 : 1 under irradiation of photolytic light of 2,000 to 5,000 A using at least 0.5 moles of halogenated hydrocarbon as a diluent per one mole of pyridine, an improvement comprising carrying out the reaction in the presence of at least 0.2 moles of water per mole of pyridine.

2. A process according to claim 1 wherein the reaction is carried out in a liquid phase.

3. A process according to claim 2 wherein 1 to 20 moles in total of the halogenated hydrocarbon and water are used per one mole of pyridine.

4. A process according to claim 3 wherein 0.2 to 5 moles of water are added per one mole of pyridine.

5. A process according to claim 4 wherein the molar ratio of pyridine to chlorine is 1.5 – 5 : 1.

6. A process according to claim 3 wherein the halogenated hydrocarbon is carbon tetrachloride, and 2 – 10 moles of carbon tetrachloride and 0.2 – 5 moles of water are used per mole of pyridine.

7. A process according to claim 6 wherein 2 to 10 moles of carbon tetrachloride and 0.5 to 3 moles of water are fed to a reactor per mole of pyridine, and the reaction is carried out by passing a chlorine gas therethrough while maintaining the content of reactor in a boiling state.

8. A process according to claim 1 wherein the reaction is carried out in a gaseous phase.

9. A process according to claim 8 wherein 1 to 20 moles in total of the halogenated hydrocarbon and water are used per mole of pyridine.

10. A process according to claim 9 wherein the molar ratio of pyridine to chlorine is 1.5 – 5 : 1.

11. A process according to claim 9 wherein the halogenated hydrocarbon is carbon tetrachloride, and 2 – 10 moles of carbon tetrachloride and 0.2 – 10 moles of water are used per mole of pyridine.

12. A process according to claim 11 wherein a gaseous mixture of pyridine and water are fed to a reactor together with vaporized chlorine and carbon tetrachloride to effect the reaction.

13. A process according to claim 12 wherein a lamp provided with light source cooler is provided in the reactor with a cooling jacket, and a vaporized mixture of pyridine and water, and carbon tetrachloride and chlorine are fed to the reactor to effect the reaction.

14. A process according to claim 12 wherein the reaction is carried out by adding water to the inside wall of the reactor and surface of the light source lamp.

15. The process of claim 1 wherein said halogenated hydrocarbon is selected from the group consisting of carbon tetrachloride, perchloroethylene, trichloroethylene, tetrachloroethylene, ethane dichloride, ethane trichloride, and tetrachlorodifluoroethane.

* * * * *